US008389680B2

(12) United States Patent
Rasi et al.

(10) Patent No.: US 8,389,680 B2
(45) Date of Patent: *Mar. 5, 2013

(54) **TREATMENT OF *ASPERGILLUS* INFECTIONS WITH ALPHA THYMOSIN PEPTIDES**

(75) Inventors: Guido Rasi, Rome (IT); Enrico Garaci, Rome (IT); Francesco Bistoni, Perugia (IT); Luigina Romani, Perugia (IT); Paolo Di Francesco, Rome (IT)

(73) Assignee: SciClone Pharmaceuticals, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/482,978

(22) Filed: May 29, 2012

(65) Prior Publication Data

US 2012/0295840 A1 Nov. 22, 2012

Related U.S. Application Data

(62) Division of application No. 10/551,341, filed as application No. PCT/US2004/009550 on Mar. 29, 2004, now Pat. No. 8,207,294.

(60) Provisional application No. 60/457,911, filed on Mar. 28, 2003.

(51) Int. Cl.
 *A61K 38/00* (2006.01)
 *A61K 38/22* (2006.01)

(52) U.S. Cl. .................. 530/324; 514/2.4; 514/12.9

(58) Field of Classification Search .................. 514/324
 See application file for complete search history.

(56) References Cited

U.S. PATENT DOCUMENTS

| 4,002,740 | A | 1/1977 | Goldstein et al. |
| 4,079,127 | A | 3/1978 | Goldstein et al. |
| 4,116,951 | A | 9/1978 | Wang |
| 4,353,821 | A | 10/1982 | Birr et al. |
| 4,374,197 | A | 2/1983 | Horecker |
| 4,612,365 | A | 9/1986 | Birr et al. |
| 5,512,656 | A | 4/1996 | Wang |
| 5,585,352 | A | 12/1996 | Goldstein et al. |
| 5,632,983 | A | 5/1997 | Hadden |
| 5,736,519 | A | 4/1998 | Deigin et al. |
| 5,888,980 | A | 3/1999 | Ripka et al. |
| 6,001,799 | A | 12/1999 | Chretien et al. |
| 8,207,294 | B2 | 6/2012 | Rasi et al. |
| 2005/0049191 | A1 | 3/2005 | Rudolph et al. |

FOREIGN PATENT DOCUMENTS

| EP | 0603305 | 5/1997 |
| EP | 0687181 | 8/2001 |
| EP | 1613340 | 5/2010 |
| WO | WO 96/15800 | 5/1996 |
| WO | WO 98/35696 | 8/1998 |
| WO | WO 9835696 A1 * | 8/1998 |

OTHER PUBLICATIONS

Ancell, C. D. et al., "Thymosin alpha-1," Am. J. Health-Syst. Pharm., 58:879-888 (2001).

Attia, W. Y. et al., "Thymosin stimulates interleukin-6 production from rat spleen cells in vitro," Immunopharmacology, 26(2):171-179 (1993).
Baxevanis, C. N. et al., "Induction of lymphokine-activated killer activity in mice by prothymosin α," Cancer Immunol. Immunother., 38(4):281-286 (1994).
Baxevanis, C. N. et al., "Enhancement of human T lymphocyte function by prothymosin α: Increased production of interleukin-2 and expression of interleukin-2 receptors in normal human peripheral blood T lymphocytes," Immunopharmacology and Immunotoxicology, 12(4): 595-617 (1990).
Baxevanis, C. N. et al., "Immunoregulatory effects of fraction 5 thymus peptides. I. Thymosin α1 enhances while thymosin β4 supresses the human autologous and allogeneic mixed lymphocyte reaction," Immunopharmacology, 13(2)133-141 (1987).
Bistoni, F. et al., "Increase of mouse resistance to *Candida albicans* infection by thymosin alpha 1," Infection and Immunity, 36(2):609-614 (1982).
Bozza, S. et al., "Dendritic Cells Transport Conidia and Hyphae of *Aspergillus fumigatus* from the Airways to the Draining Lymph Nodes and Initiate Disparate Th Responses to the Fungus," Journal of Immunology, American Association of Immunologists, 168(3):1362-1371 (2002).
Di Francesco et al., "Combined Effect of Fluconazole and Thymosin α1 on Systemic Candidiasis in Mice Immunosuppressed by Morphine Treatments," Clin. Exp. Immunol., 97:347-352 (1994).
Giuliani, C. et al., "Thymosin-alpha1 regulates MHC class I expression in FRTL-5 cells at transcriptional level," Eur. J. Immunol, 30:3:778-786 (2000).
Goldstein, A. L. et al., "From lab to bedside: emerging clinical applications of thymosin $α_1$," Expert Opinion Biol. Ther., 9(5):593-608 (2009).
Goldstein, A.L. et al., "Purification and Biological Activity of Thymosin, a Hormone of the Thymus Gland," Proc. Nat'l Acad. Sci. (USA), 69(7):1800-1803 (1972).
Knutsen, A. P. et al., "Thymosin-$α_1$ stimulates maturation of CD34+ stem cells into CD3+4+ cells in an in vitro thymic epithelia organ coculture model," International Journal of Immunopharmacology, 21(1):15-26 (1999).
Kouttab, N. M. et al., "Production of human B and T cell growth factors is enhanced by thymic hormones," Immunopharm., 16(2):97-105 (1988).
Lasso-Floral, "Pulmonary *aspergillus* colonization in humans and its impact on management of critically ill patients," British Journal of Hematology, 104:745-747 (1999).
Leichtling, K. D. et al., "Thymosin alpha 1 modulates the expression of high affinity interleukin-2 receptors on normal human lymphocytes," International Journal of Immunopharmacology, 12(1):19-29 (1990).
Marshall, G. D. et al., "In vivo generation of suppressor T cells by thymosin in congenitally athymic nude mice," The Journal of Immunology, 126(2):741-744 (1981).
MedlinePlus—*Aperilligus* Symptoms, http:www.nlm.nih.gov/medlineplus/ency/article/001326.htm.

(Continued)

*Primary Examiner* — Christina Bradley
*Assistant Examiner* — Jeanette Lieb
(74) *Attorney, Agent, or Firm* — Cooley LLP

(57) ABSTRACT

A method for treating a human infected with *Aspergillus* by using thymosin alpha 1 as an immuno-stimulator in activating dendritic cells. The method is particularly useful in preventing an infection by *Aspergillus* in an immuno-compromised host being treated with a bone marrow transplantation.

21 Claims, No Drawings

OTHER PUBLICATIONS

Naylor, P. H. et al., "T cell targeted immune enhancement yields effective T cell adjuvants," Intl Immunopharmacol., 3(8):1205-1215 (2003).

Ohmori, H. et al., "Restoration of immunocyte functions by thymosin alpha 1 in cyclophosphamide-induced immunodeficient mice," Immunopharmacol Immunotoxicol, 23(1):75-82 (2001).

Ohta, Y. et al., "Immunomodulating activity of thymosin fraction 5 and thymosin $\alpha_1$ in immunosuppressed mice," Cancer Immunol. Immunother., 15(2):108-113 (1983).

Oren, I. et al., "Invasive Pulmonary Aspergillosis," Current Opinion in Pulmonary Medicine, 8(3):195-200 (2002).

Pozo, D. et al., "Thymosin $\alpha 1$ Interacts with the VIP receptor-effector system in rat and mouse immunocompetent cells," Immunopharmacology, 34:113-123 (1996).

Roilides, E. et al., "Tumor Necrosis Factor Alpha Enhances Antifungal Activities of Polymorphonuclear and Mononuclear Phagocytes against *Aspergillus fumigatus*," Infection and Immunity, 66(12):5999-6003 (1998).

Romani, L. et al., "Thymosin $\alpha$ 1 activates dendritic cells for antifungal Th1 resistance through toll-like receptor signaling," Blood, 103(11):4232-4239 (2004).

Romani, L. et al., "Thymosin alpha 1: An Endogenous Regulator of Inflammation, Immunity, and Tolerance," Ann. N.Y. Acad. Sci., 1112:326-338 (2007).

Serrate, S. A., et al., "Modulation of human natural killer cell cytotoxic activity, lymphokine production, and interleukin 2 receptor expression by thymic hormones," J. Immunol., 139(7):2338-2343 (1987).

Shoman, S. et al., "The immune response to fungal infections," Br. J. Haematology, 129:569-582 (2005).

Svedersky, L. P. et al., "Induction and augmentation of mitogen-induced immune interferon production in human peripheral blood lymphocytes by N alpha-desacetylthymosin alpha 1," Eur. J. Immunol., 12(3):244-247 (1982).

Sztein, M. B. et al., "Modulation of interleukin 2 receptor expression on normal human lymphocytes by thymic hormones," Proc Natl. Acad Sci USA, 83:6107-6111 (1986).

Wingard, J. R., "Efficacy of amphotericin B lipid complex injection (ABLC) in bone marrow transplant recipients with life-threatening systemic mycoses," Bone Marrow Transplantation, 19:343-347 (1997).

Office Action for Chinese Application No. 200480008490.4 issued Sep. 22, 2006.

Supplemental European Search Report for European Application No. 04749495 issued Jun. 2, 2009.

Office Action for Israel Application No. 171118 issued Nov. 19, 2008.

Office Action for Japanese Application No. 509423-2006 issued Mar. 2, 2010.

Office Action for Mexican Application No. MX/a/2005/010391 issued Jul. 7, 2010.

Office Action for Norwegian Application No. 20054912 issued Apr. 28, 2010.

Office Action for New Zealand Application No. 542900 issued Aug. 9, 2006.

International Search Report and Written Opinion for International Application No. PCT/US2004/009550 mailed Oct. 15, 2004.

Office Action for Singapore Application No. 2005061452 issued Mar. 12, 2007.

Office Action for Singapore Application No. 2005061452 issued Nov. 3, 2006.

Office Action for U.S. Appl. No. 10/551,341 mailed Aug. 4, 2011.

Office Action for U.S. Appl. No. 10/551,341 mailed Apr. 6, 2009.

Office Action for U.S. Appl. No. 10/551,341 mailed Sep. 28, 2009.

* cited by examiner

SEQUENCE LISTING

<160> NUMBER OF SEQ ID NOS: 2

<210> SEQ ID NO 1
<211> LENGTH: 27
<212> TYPE: PRT
<213> ORGANISM: Unknown
<220> FEATURE:
<223> OTHER INFORMATION: Thymosin alpha 1 peptide
<220> FEATURE:
<221> NAME/KEY: MISC_FEATURE
<222> LOCATION: (1)..(1)
<223> OTHER INFORMATION: May be acetylated

<400> SEQUENCE: 1

Ser Asp Ala Ala Val Asp Thr Ser Ser Glu Ile Thr Thr Lys Asp Leu
1               5                   10                  15

-continued

```
Lys Glu Lys Lys Glu Val Glu Glu Ala Glu Asn
            20                  25

<210> SEQ ID NO 2
<211> LENGTH: 28
<212> TYPE: PRT
<213> ORGANISM: Unknown
<220> FEATURE:
<223> OTHER INFORMATION: Thymosin alpha 1 peptide
<220> FEATURE:
<221> NAME/KEY: MISC_FEATURE
<222> LOCATION: (1)..(1)
<223> OTHER INFORMATION: May be acetylated

<400> SEQUENCE: 2

Ala Lys Ser Asp Val Lys Ala Glu Thr Ser Ser Glu Ile Asp Thr Thr
1               5                   10                  15

Glu Leu Asp Glu Lys Val Glu Val Lys Ala Asn Glu
            20                  25
```

TREATMENT OF *ASPERGILLUS* INFECTIONS WITH ALPHA THYMOSIN PEPTIDES

CROSS-REFERENCE TO RELATED APPLICATIONS

This application is a Divisional of U.S. application Ser. No. 10/551,341, filed Nov. 20, 2006, now U.S. Pat. No. 8,207,294, which is a National Phase entry under 35 U.S.C. 371 of PCT/US2004/009550, filed Mar. 29, 2004, which claims the benefit of provisional application 60/457,911 filed Mar. 28, 2003.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: SCIC_050_02US_SeqList_ST25.txt, date recorded: Aug. 7, 2012, file size 2 kilobytes).

FIELD OF THE INVENTION

The present invention relates to the treatment of fungal infections. In particular the present invention relates to the treatment and prevention of *Aspergillus* infections such as Invasive Aspergillosis associated with bone marrow transplantations.

BACKGROUND OF THE INVENTION

Invasive aspergillosis (IA), characterized by hyphal invasion, destruction of pulmonary tissue and dissemination to other organs, is the leading cause of both nosocomial pneumonia and death in allogeneic bone marrow transplantation (BMT) with an estimated infection rate of 5 to 10% and an associated mortality rate of 90 to 100%. The most important risk factor for IA has historically been neutropenia, such that reconstitution with myeloid progenitors offered protection against IA in a murine model of allogeneic BMT. However, recent studies on the epidemiology of IA in BMT recipients indicated a reduced neutropenia-related infection and an increase "late-onset" infection, in concomitance with the occurrence of graft versus host disease.

There is a need in the art for methods of treating *Aspergillus* infection.

SUMMARY OF THE INVENTION

In accordance with the present invention, a method for treating or preventing an *Aspergillus* infection in a mammal comprises administering to the mammal a pharmaceutical composition comprising an antifungal effective amount of thymosin alpha 1 (TA1).

DETAILED DESCRIPTION OF THE INVENTION

Clinical and experimental evidence suggest a role of a Th1 cell reactivity in the control of IA. Dendritic cells (DCs) instruct Th1 priming to the fungus in vivo and in vitro. Evidence indicates that the ability of pulmonary DCs to instruct the appropriate T cell responses to fungal antigens may be affected by local immuno-regulatory events, including signaling through Toll-like receptors (TLRs). DCs may be promising targets for intervention for immunotherapy and vaccine development, and shifts the focus of pharmaceutical intervention towards an "adjuvant". An adjuvant which is capable of both stimulating the appropriate type of response best tailored to combating the infection and being effective in conditions of immunosuppression is advantageous.

Thymosin alpha 1 (TA1) is a naturally occurring thymic peptide. In the form of a synthetic 28-amino acid peptide, TA1 is in clinical trials worldwide for the treatment of some viral infections, either as monotherapy or in combination with interferon alpha. The treatment of some immunodeficiencies, malignancies and HIV/AIDS are additional indications for TA1. The mechanism of action of a synthetic polypeptide of TA1 is not completely understood but is thought to be related to its immuno-modulating activities, centered primarily on the augmentation of T-cell function. Because of its immuno-modulatory function on cells on the innate immune system, including the ability to activate mitogenactivated protein kinases (MAPKs) and gene expression on macrophages, we have considered TA1 as an adjuvant capable of activating DCs for Th1 priming to *Aspergillus*. The present invention provides a treatment of *Aspergillus* infections wherein TA1 may activate DCs for antifungal Th1 priming by signaling through TLRs.

The present invention provides a method for treating a mammal infected with *Aspergillus* comprising administering an antifungal effective amount of TA1 to such a mammal. In a preferred embodiment TA1 is effective against Invasive Aspergillosis (IA). The effective dose of TA1 is sufficient to activate dendritic cells to produce Th1 cell promoting cytokines. A preferred dose for treating the fungal infection is in the range between 200 and 400 micrograms/kg body weight per day. In a preferred embodiment the mammal is an immuno-compromised host, particularly a human. The method is particularly useful in treating immuno-comprised patients, specifically those patients who are bone marrow transplantation recipients.

The present invention also provides a method for preventing an *Aspergillus* infection in a mammal comprising administering to such mammal an antifungal effective amount of TA1. The invention is particularly useful in preventing IA in an immuno-compromised host. In a preferred embodiment the method prevents such infection in immuno-compromised patients, specifically those patients being bone marrow transplantation recipients. The effective dose of TA1 is sufficient to activate dendritic cells to produce Th1 cell promoting cytokines. A preferred dose for preventing the fungal infection is in the range between 200 and 400 micrograms/kg body weight per day.

Without being bound to any particular theory, it is believed that the present invention is based on the discovery of a novel immuno-regulatory activity of TA1 for the treatment of or protection against an *Aspergillus* infection. TA1 appears to promote the production of the Th1-promoting cytokines IL-12 p70, IL-10, and IFN-alpha, in various types of DCs through a MyD88-dependent pathway.

In TLR-transfected cells, TA1 appears to directly activate TLR9 but not TLR2 signaling, the last being potentiated in response to relevant ligands. Therefore, TA1 appears to activate TLR signaling either directly or indirectly. The data suggest that TA1 may use the TLR2-dependent pathway on myeloid dendritic cells (MDCs) for IL-12 p70 production and the TLR9-dependent pathway on plasmacytoid dendritic cells (PDCs) for IFN-alpha and IL-10 production.

As IL-10 production by DCs may be a component of memory protective antifungal immunity, balancing the IL-12/

IL-10 production on DCs and/or different DC subsets may be a reason for the very essence of adjuvanticity of TA1 in Aspergillosis.

In a BMT mouse model, TA1 treatment after *Aspergillus* infection led to an increase in $CD4^+$ and $CD8^+$ cells, as well as an increase in total neutrophils. The frequency of Th1 cells (producing IFN-gamma) were increased, while the Th2 cells (producing IL-4) were decreased after treatment with TA1.

Importantly, treatment of BMT mice infected with *Aspergillus* with TA1 led to a dose-responsive reduction in fungal growth in the lungs, and at the higher doses was able to affect a complete cure of the infection. TA1 was also able to increase the therapeutic efficacy of amphotericin B.

The effects of TA1 on DCs are consistent with its anti-apoptotic activity. Since DCs are central in the balancing act between immunopathology, immunity and autoimmunity, and PDCs signaling through TLR9 are present in the thymus, the ability to modulate DC functioning indicates that TA1 is an endogenous regulator of the innate and adaptive immune systems acting through TLR utilization. This provides a rationale for the therapeutic prescription of TA1 in some viral infections, where PDCs producing IFN-alpha are considered to play a central role. For the production of IFN-alpha in these PDCs, TLR9 is essentially required. Moreover, PDCs appear also to participate in immune responses after hematopoietic cell transplantation, which may explain, among others, the beneficial effect of TA1 in the immuno-reconstitution in BMT mammals.

TLRs appear to activate the innate immune system not only to assist the adaptive immune system but also for direct antimicrobial effector activity. Since TA1 appears to activate DCs for Th1 priming to *Aspergillus*, and also effector neutrophils to an antifungal state, this further indicates the beneficial effect in the treatment of fungal infections by TA1.

*Aspergillus* has a unique nature, in that it is a saprophytic fungus colonizing immunocompromised hosts. The present invention provides deliberate targeting of cells and pathways of cell-mediated immunity and increases resistance to *Aspergillus*, wherein TA1 is the adjuvant programming the appropriate Th1 reactivity to the fungus through utilization of the TLR pathway.

The invention is further illustrated by the following example, which is not to be construed as limiting.

Example 1

Animals

Female, 8- to 10-weeks old, BALB/c and C57BL6 mice were from Charles River. NOD/SCID were from The Jackson. Breeding pairs of homozygous TLR2-, TLR9- and MyD88-deficient mice, raised on C57BL6 background, and of homozygous IFN-gamma- and IL-4-deficient mice, raised on BALB/c background, were bred under specific-pathogen free conditions.

Microorganism Infections and Treatments

For infection with *A. fumigatus*, mice were intranasally injected for 3 consecutive days with a suspension of $2 \times 10^7$ conidia/20 microliter saline. For the quantification of fungal growth in the lungs, the chitin assay was used. The chitin content was expressed as micrograms of glucosamine per organ. The glucosamine content of lungs from uninfected mice was used as a negative control ranging between 0.80 and 2.25 microgram glucosamine/organ. For histological analysis, lungs were excised and immediately fixed in formalin. Sections (3 to 4 micron) of paraffin-embedded tissues were stained with the periodic acid-Schiff procedure. Thymosin alpha 1 (TA1) and the scrambled polypeptide are as purified sterile lyophilized acetylated polypeptides with endotoxin levels less than 0.03 pg/ml, by a standard limulus lysate assay. The sequences were as follows: Ac-Ser-Asp-Ala-Ala-Val-Asp-Thr-Ser-Ser-Glu-Ile-Thr-Thr-Lys-Asp-Leu-Lys-Glu-Lys-Lys-Glu-Val-Glu-Glu-Ala-Glu-Asn-O (Thymosin alpha 1, SEQ ID NO.: 1) and Ac-Ala-Lys-Ser-Asp-Val-Lys-Ala-Glu-Thr-Ser-Ser-Glu-Ile-Asp-Thr-Thr-Glu-Leu-Asp-Glu-Lys-Val-Glu-Val-Lys-Ala-Asn-Glu-OH (Thymosin alpha 1, SEQ ID NO.: 2). Their lyophilized powders were reconstituted in sterile water.

The treatments were as follows; in BMT-mice, TA1, at different doses administered intraperitoneally, sthymosin alpha 1, 400 microgram/kg administered intraperitoneally or human recombinant G-CSF 250 microgram/kg administered intravenously, were given daily beginning the day of the BM infusion, in concomitance with the infection and continuing for an additional 3 days. Amphotericin B was given daily for 3 days in concomitance with the infection, at a dose of 4000 microgram/kg, administered intraperitoneally. This dose would cure IA in cyclophosphamide-treated mice. Cyclophosphamide, 150 mg/kg administered intraperitoneally, was given a day before the infection. In cyclophosphamide-treated mice, 400 microgram/kg TA1 was given intraperitoneally for 5 consecutive days beginning the day of the infection.

Neutrophil depletion was obtained by treatment with 1 mg of Gr-1-neutralizing RB6-8C5 antibody intravenously, a day before and after the infection. The treatment dramatically reduced the number of lung neutrophils but not that of DCs (between 5 to $6 \times 10^5$ $CD11c^+$, MHC Class $II^+$, F480-cells before and after treatment). Control mice received an equivalent amount of purified rat IgG2b. FACS analysis of lung cells a day after treatment with cyclophosphamide revealed a profound and long-lasting (for up to 5 days) leukopenia. The percentages of $F480^+$ cells (about 20%) and that of $CD11c^+$, MHC Class $II^+$, F480-DCs (<3%) were unaffected by treatment.

TLR Ligands

Zymosan was from *Saccharomyces cerevisiae*, lipoteichoic acid (LTA) from *Staphylococcus aureus*, and lipopolysaccharide (LPS) from *Salmonella Minnesota* Re 595. The CpG oligonucleotides 1826 and 2006 were proven immunostimulatory sequences.

Generation of BMT Mice

C57BL6 mice were exposed to a lethal dose of 9 Gy and infused with T cell-depleted donor cells from BALB/c mice. More than 95% of the mice survived showing stable, donor type hematopoietic chimerism, as revealed by donor type MHC class I antigen expression on cells from spleens.

Dendritic Cell Isolation and Culture

Blood $CD 11c^+$ myeloid DCs (MDCs) were generated from $CD 14^+$ mononuclear cells by magnetic cell sorting and cultured for 5 days in Iscove's modified medium, containing 10% fetal bovine serum, 50 micromolar 2-mercaptoethanol, sodium pyruvate (1 mM), 2 mM L-glutamine, HEPES (10 mM), and 50 micrograms/ml gentamycin in the presence of 50 ng/ml rHuman GM-CSF and 200 U/ml rHuman IL-4. Immature MDCs were cultured for 24 hours with 1000 ng/ml trimeric human CD40 ligand-leucine-zipper fusion protein to obtain mature DCs. $CD 123^+$ plasmacytoid DCs (PDCs) were isolated using the BDCA-4 isolation kit. Purity of $CD 123^+$ cells was >96%.

For mature PDCs, immature DCs were cultured with the trimeric human CD40 ligand as above and 10 ng/ml IL-3. FACS analysis revealed that PDCs were $CD123^{bright}$, $CD4^+$, $CD45RA^+$ and $CD11c^-$ as opposed to MDCs characterized as being $CD1a^+$, $CD11c^+$, $CD11b^+$, $CD4^+$, $CD14^{low}$ and $CD8^-$.

The expression of HLA Class II, CD80 and CD86 was high in both immature and mature DCs. Murine lung CD 11c+ DCs (between 5 to 7% positive for CD8alpha and between 30 to 35% positive for Gr-1) were isolated by magnetic cell sorting.

For phagocytosis, DCs were pre-exposed to 100 ng/ml TA1 for 60 minutes and subsequently incubated at 37° C. with *Aspergillus conidia* for an additional 60 minutes. The percentage of internalization was calculated and photographs were taken. In assessing functional maturation and cytokine determination, purified DCs were resuspended in Iscove's medium (with no serum but with polymixin B, to avoid non-specific activation by serum components and endotoxin) and pulsed with 100 ng/ml TA1 for 24 hours either alone or together with TLR ligands or unopsonized *Aspergillus conidia*.

Phenotypic Analysis

Cell surface phenotype was assessed by reacting samples with FITC- or PE-conjugated rat anti-mouse antibodies. Unrelated hisotype matched antibodies were used as control.

Antifungal Effector Activity

In determining phagocytosis, bronchoalveolar macrophages and peripheral neutrophils were pre-exposed to 100 ng/ml TA1 for 60 minutes and incubated at 37° C. with unopsonized *Aspergillus conidia* for 60 minutes. In addition, the conidiocidal activity was assessed by determining the number of colony forming units and the percentage of colony forming units inhibition (mean±SE), referred to as conidiocidal activity.

Assay with HEK293 Transfected Cells.

The human embryonic kidney cell line HEK293, wild type or stably transfected with human TLR2, TLR9 and TLR4/CD1427 were cultured in low glucose Dulbecco's modified Eagle's medium supplemented with 10% FCS, HEPES (10 nM), L-glutamine (2 microgram/ml), and gentamycin (50 microgram/ml). Transfectants were additionally supplemented with puromycin (100 microgram/ml). For stimulation experiments, cells were cultured at a density of 3 to $5 \times 10^5$ cells/wells in 12-well tissue culture plates overnight. Cells were washed and stimulated with 100 ng/ml TA1 either alone or together with TLR ligands for 5 h before the assessment of IL-8 production in the supernatants.

Cytokine and Spot Enzyme-Linked Immunosorbent (ELISPOT) Assay

The levels of TNF-alpha, IL-10, IL-12 p70, IFN-alpha and IL-8 in culture supernatants were determined by Kit ELISAs. The detection limits (pg/ml) of the assays were <3 (human) and <32 (murine) for TNF-alpha, <12 (murine) and <5 (human) for IL-10, <16 (murine) and <3 (human) for IL-12 p70 and <25 (human) IL-8. For human IFN-alpha <3 ng/ml. For enumeration of cytokine-producing cells, an ELISPOT assay was used on purified CD4+ T cells and DCs from lungs.

Proliferation Assay by Flow Cytometric Analysis

Proliferation of lung CD4+ T lymphocytes stimulated with 10 microgram/ml Con A or heat inactivated *conidia* in the presence of lung DCs, was assessed by labeling with CFSE 5(6)-carboxyfluorescein diacetate succinimidyl ester.

Reverse Transcriptase (RT)-PCR

Total RNA was extracted from immature DCs pre-treated with 100 ng/ml TA1 for 60 minutes followed by the exposure to unopsonized *Aspergillus conidia* for 60 minutes, as suggested by initial experiments. Synthesis and PCR of cDNA were performed with forward and reverse PCR primers and the cycles used for murine and human TLRs and HPRT. The synthesized PCR products were separated by electrophoresis on 2% agarose gel and visualized by ethidium bromide staining.

Analysis of p38 and NF-KB Activation

P38 and NF-kB were activated on lung DCs by exposure for 20 minutes at 37° C. to *Aspergillus conidia* and/or 100 ng/ml TA1. Blots of cell lysates were incubated with rabbit polyclonal Abs recognizing either the unphosphorylated form of p38 MAPK, or the double-phosphorylated (Thr-180/Tyr-182) p38 MAPK, or Abs specific for the Rel A, 65 kDa DNA binding subunit of human NF-kB followed by horseradish peroxidase-conjugated goat anti-rabbit IgG, as per manufacturer's instructions. Blots were developed with an Enhanced Chemiluminescence detection kit. Bands were visualized after exposure of the blots to a Kodak RX film. To ensure similar protein loading in each lane, the phospho blots were stripped and the membranes were reprobed with Abs against p38 and NF-kB.

Thymosin Alpha 1 (TA1) Activates Dendritic Cells (DCs)

Previously it has been shown that murine DCs phagocytose *Aspergillus* in vitro and at the site of infection. TA1, but not the scrambled peptide activates lung DCs for phagocytosis of unopsonized *conidia* (more than hyphae), costimulatory antigen expression and cytokine production. In contrast, *Aspergillus conidia* alone does not represent a sufficient stimulus to induce the activation of DCs, but the combined exposure to TA1 remarkably increased the expression of MHC Class II antigens, CD86 and CD40 molecules and the frequency of IL-12 p70-producing DCs. Interestingly, IL-12 p70-producing DCs are also increased by thymosin alone. TA1 also activates human MDC and PDC subsets. Both immature and mature DC subsets phagocytose *conidia*. TAI increased the phagocytic activity of immature DCs, affects the DC morphology (more cytoplasmic projections can be detected in immature MDCs) and up-regulate the HLA Class II antigens and costimulatory molecule expression in response to *conidia*. TA1 significantly increase the release of IL-12 p70 in response to *conidia* and to zymosan by immature MDCs and that of IL-10 in response to canidia by immature PDCs. IFN-alpha can be produced by PDCs in response to the TLR9 ligand CpG, which production is significantly potentiated by TA1. In contrast, the scrambled peptide failed to up-regulate Class II antigens and costimulatory molecule expression and to induce cytokine production by DCs in response to *conidia*.

Together, these data point to a novel, previously undefined, immuno-regulatory role for TA1 in the activation and functioning of DCs.

TA1 Activates the MyD88-Dependent Pathway Through TLR Signaling

TLR signaling occurred in response to *Aspergillus conidia*, which mediates functional responses to the fungus. TA1 strongly activates the expression of TLR2, TLR5, and TLR9 on murine DCs TLR2 and TLR9 are still activated upon the combined exposure to *conidia* and TA1, whereas the expression of TLR5, whose expression is inhibited. Again, the scrambled peptide failed to activate TLR2 and TLR9 expression either alone or in response to *conidia*.

The ability of TA1 to activate TLR-dependent signaling is supported by studies in HEK293 cells transfected with TLR2, TLR9 and TLR4/CD14 by determining the IL-8 production in response to TA1 alone or together with the relevant TLR ligands. In such HEK293 cells TA1 significantly increased the production of IL-8 by TLR9-transfected cells either alone or in response to the TLR9 ligand CpG. However, TA1 did not stimulate the production of IL-8 by TLR2-transfected cells alone but slightly increased the production of IL-8 in these cells in response to zymosan. Furthermore, TA1 did not induce IL-8 in TLR4/CD14-transfected cells either alone or in response to the TLR4 ligand LPS. TA1 also affects the ability of murine DCs to produce IL-12 p70 and IL-10 in response to these microbial TLR ligands. TA1 did not affect cytokine production in response to Poly(I:C) or LPS (TLR4), TA1 significantly increased the production of IL-12 p70 and decreases that of IL-10 after stimulation with zymosan and LTA (TLR2) and CpG (TLR9). Therefore, TA1 appears to be able to signal directly through TLR9 and to potentiate TLR2 signaling by the relevant ligand.

Both NF- and p38 MAPK activation are early events in triggering TLR-induced gene expression, and TA1 has been previously shown to activate MAPK-transduction pathways. In support of its involvement in the TLR-induced pathways, TA1 induced the nuclear translocation of NF-kB as well as p38 phosphorylation (which were not stimulated by either conidia alone, the scrambled peptide, or the scrambled peptide plus conidia). Furthermore, inhibitors of NF-kB nuclear translocation (SN50) or p38 MAPK (SB202190) ablate the effect of TA1 on DCs.

The myeloid differentiation factor 88 (MyD88) is one of the adaptor protein essential for the activation of NF-kB and MAPK and the production of IL-12 p70 upon signaling by TLRs. The effect of TA1 and conidia on IL-12 p70 production, and the effect of TAI1 on IL-10 production are dramatically ablated in MyD88-deficient mice. Therefore, the MyD88-dependent pathway appears to play an essential role in the mechanism of action of TA1 in vitro. To determine whether the MyD88-dependent pathway plays an essential role in TA1 action in vivo as well. Local fungal growth was assessed after infection of wild type. TLR2-, TRL9- or MyD88-deficient mice with Aspergillus. Fungal growth in TLR2- and TLR9-deficient mice was comparable to that of wild type mice and it is similarly impaired upon thymosin treatment. Fungal growth is comparable MyD88-deficient mice as well, but in these mice it was not impaired upon treatment with TA1. Thus, despite a degree of redundancy in the TLR usage, the MyD88-dependent signaling pathway appears to be essential for in the activity of TA1 both in vitro and in vivo.

TA1 Protects BMT-Mice from IA

Treatment with TA1, but not with the scrambled peptide, appeared to be able to cure BMT mice with IA, as revealed by increased survival that parallels reduced fungal growth in the lungs. The effect on protection is dose-dependent full protection (>60 d survival) being achieved in mice treated with 200 and 400 microgram/kg TA1 and is superior to that of amphotericin B. Moreover, TA1 increases the therapeutic efficacy of amphotericin B, as indicated by the increased survival and decreased fungal burden of mice treated with both agents. Furthermore, TA1 also decreases lung pathology. Lung sections from infected mice show the presence of numerous Aspergillus hyphae infiltrating the lung parenchyma, with severe signs of bronchial wall damage and necrosis and scarce inflammatory cell recruitment. In contrast, these features are not observed in TA1 treated mice, whose lungs are characterized by healing infiltrates of inflammatory cells with no evidence of fungal growth and bronchial wall destruction. Thus, TA1 may have therapeutic efficacy in IA and may be beneficial in combination with antifungals known to have a reduced activity in BMT settings.

TA1 Accelerates Myeloid and Th1 Cell Recovery in Mice with IA

The absolute number of circulating lymphocytes and neutrophils significantly increases after TA1 treatment. More importantly, as blood neutrophil levels do not predict susceptibility to aspergillosis. In cytofluorimetric analysis however the numbers of lung $CD4^+$ and $CD8^+$ cells and neutrophils were significantly increased upon treatment of BMT mice with TA1. These lung $CD4^+$ T lymphocytes are functionally active as indicated by antigenspecific proliferation and IFN-gamma production. The frequency of Th1 cells (producing IFN-gamma) producing cells is higher, and Th2 cells (producing IL-4) is lower in mice treated with TA1. Further, the with respect to antifungal activity of effector phagocytes, the conidiocidal activity of both macrophages and neutrophils is higher in TA1 treated mice. Therefore, TA1 appears to not only promote DC maturation but also to activate local effector cells for prompt phagocytosis and killing of the fungus.

Recovery from neutropenia alone, for example by treatment with a dose of G-CSF known to accelerate neutrophil recovery in mice, is not sufficient to mediate a degree of antifungal resistance comparable to that obtained with TA1. Similarly, despite a significant neutrophil recovery, the therapeutic efficacy of TA1 in mice devoid of T cells or IFN-gamma-producing Th1 cells is not as great. Furthermore, improved therapeutic efficacy of TA1 is achieved in the presence of increased Th1 cells, such as that occurring in IL-4-deficient mice. Therefore, although neutrophils play an essential role in medicating antifungal resistance in the absence of an adaptive Th1-dependent immunity, the achievement of a state of full protection to the fungus, as appears to be obtained by treatment with TA1, may rely on the coordinated action between innate effector phagocytes and protective Th1 cells.

The invention claimed is:

1. A method of treating a fungal infection in a bone marrow transplant recipient comprising administering to said transplant recipient in need thereof a pharmaceutical composition comprising an antifungal effective amount of thymosin alpha 1 (TA1), wherein the antifungal effective amount of thymosin alpha 1 (TA1) induces activity selected from p38 activation, NFkB activation, TLR signaling, MyD88 signaling and dendritic cell activation.

2. The method according to claim 1, wherein said TA1 is administered at a dose of 200 to 400 micrograms/kg body weight/day.

3. The method according to claim 1, wherein the TLR signaling induced results in dendritic cell activation.

4. The method according to claim 3, wherein the dendritic cells are selected from plasmocytoid dendritic cells (PDCs) and myeloid dendritic cells (MDCs).

5. The method according to claim 1, wherein the MyD88 signaling induced results in dendritic cell activation.

6. The method according to claim 1, wherein said TA1 is administered at a dose sufficient to produce Th1 cell promoting cytokines.

7. The method according to claim 6, wherein the Th1 cell promoting cytokines are selected from IL-12 p70, IL-10 and IFN-alpha.

8. The method according to claim 1, wherein the p38 activation induced is phosphorylation of p38.

9. The method according to claim 1, wherein the NFkB activation induced is nuclear translocation of NFkB.

10. The method according to claim 1, wherein said TLR signaling is selected from TLR9 signaling and TLR2 signaling.

11. The method according to claim 10, wherein said TLR9 signaling results in IL-12 p70 production.

12. The method according to claim 10, wherein said TLR9 signaling results in activation of plasmocytoid dendritic cells (PDCs).

13. The method according to claim 10, wherein said TLR2 signaling results in IL-10 and IFN-alpha production.

14. The method according to claim 10, wherein said TLR2 signaling results in activation of myeloid dendritic cells (MDCs).

15. The method according to claim 1, wherein the antifungal infection is an *Aspergillus* infection.

16. The method according to claim 15, wherein said *Aspergillus* infection is Invasive Aspergillosis.

17. The method according to claim 1, wherein said bone marrow transplant recipient is a mammal.

18. The method according to claim 1, wherein said bone marrow transplant recipient is a human.

19. The method according to claim 1, wherein the method further comprises administering to said recipient at least one additional antifungal agent.

20. The method according to claim 19, wherein the additional antifungal agent is Amphotericin B.

21. The method according to claim 20, wherein said Amphotericin B is administered at a dose of 4000 micrograms/kg body weight/day.

* * * * *